(12) United States Patent
Toshihiko et al.

(10) Patent No.: US 11,197,805 B2
(45) Date of Patent: Dec. 14, 2021

(54) COSMETIC SUNSCREEN STICK

(71) Applicant: BEIERSDORF AG, Hamburg (DE)

(72) Inventors: Shimoda Toshihiko, Tokyo (JP); Katrin Weinert, Hamburg (DE); Andreas Bleckmann, Ahrensburg (DE)

(73) Assignee: BEIERSDORF AG, Hamburg (DE)

( * ) Notice: Subject to any disclaimer, the term of this patent is extended or adjusted under 35 U.S.C. 154(b) by 0 days.

(21) Appl. No.: 16/483,454

(22) PCT Filed: Jan. 30, 2018

(86) PCT No.: PCT/EP2018/052206
§ 371 (c)(1),
(2) Date: Aug. 5, 2019

(87) PCT Pub. No.: WO2018/145943
PCT Pub. Date: Aug. 16, 2018

(65) Prior Publication Data
US 2020/0030197 A1    Jan. 30, 2020

(30) Foreign Application Priority Data
Feb. 8, 2017  (DE) ......................... 102017201947.6

(51) Int. Cl.
*A61K 8/02* (2006.01)
*A61K 8/25* (2006.01)
*A61K 8/29* (2006.01)
*A61K 8/34* (2006.01)
*A61K 8/37* (2006.01)
*A61K 8/49* (2006.01)
*A61K 8/891* (2006.01)
*A61K 8/92* (2006.01)
*A61Q 17/04* (2006.01)

(52) U.S. Cl.
CPC .............. *A61K 8/0229* (2013.01); *A61K 8/25* (2013.01); *A61K 8/29* (2013.01); *A61K 8/342* (2013.01); *A61K 8/37* (2013.01); *A61K 8/4966* (2013.01); *A61K 8/891* (2013.01); *A61K 8/92* (2013.01); *A61K 8/922* (2013.01); *A61Q 17/04* (2013.01); *A61K 2800/30* (2013.01)

(58) Field of Classification Search
None
See application file for complete search history.

(56) References Cited

U.S. PATENT DOCUMENTS

| | | | | |
|---|---|---|---|---|
| 5,667,765 A * | 9/1997 | Hansenne | ................ | A61K 8/35 424/400 |
| 2003/0012764 A1 * | 1/2003 | Collin | .................... | A61K 8/922 424/78.17 |
| 2005/0257335 A1 * | 11/2005 | Dumousseaux | ......... | A61K 8/19 8/406 |
| 2007/0009453 A1 | 1/2007 | Willemin | | |
| 2011/0045036 A1 * | 2/2011 | Lintner | .................. | A61Q 19/00 424/401 |
| 2011/0305650 A1 * | 12/2011 | Herzog | .................... | A61K 8/37 424/59 |
| 2012/0134943 A1 | 5/2012 | Syed | | |
| 2015/0004109 A1 * | 1/2015 | Kurkal-Siebert | ........ | A61K 8/37 424/60 |
| 2015/0166909 A1 * | 6/2015 | Loudon | ................ | B01D 9/0027 208/27 |

FOREIGN PATENT DOCUMENTS

| | | | |
|---|---|---|---|
| DE | 102015203509 A1 | 9/2016 | |
| WO | 2008009562 A1 | 1/2008 | |
| WO | 2010129321 A2 | 11/2010 | |
| WO | 2011061864 A1 | 5/2011 | |

OTHER PUBLICATIONS

Database GNPD [Online] MINTEL; May 2015 (May 2015). "Sun Protect Waterproof Lip Balm SPF 30".
Database GNPD [Online] MINTEL; Feb. 2015 (Feb. 2015). "Sun Protect Lip Balm SPF 30".
Database GNPD [Online] MINTEL; Sep. 2010 (Sep. 2010). "Sun Protect Lip Balm SPF 30".
Database GNPD [Online] MINTEL; Nov. 2007 (Nov. 2007). "Lip Plump Care".
Database GNPD [Online] MINTEL; Jan. 2013 (Jan. 2013). "Cushiony Essential Gloss".
Database GNPD [Online] MINTEL; Jun. 2009 (Jun. 2009). "Sun Lip Balm SPF 25".
Database GNPD [Online] MINTEL; Nov. 2016 (Nov. 2016). "Gourmand Apricot Fruity Lip Care".
Database GNPD [Online] MINTEL; Jun. 2013 (Jun. 2013). "Shimmer & Shine Lip Gloss".
Database GNPD [Online] MINTEL; Mar. 2006 (Mar. 2006). "Plumping Lip Gloss".
Database GNPD [Online] MINTEL; Mar. 2012 (Mar. 2012). Natural Rosy Gloss.
Database GNPD [Online] MINTEL; Jan. 2017 (Jan. 2017). Velvet Luminous Matte Lip Colour.
Lipstick SPF 17/PA+++. Jan. 2017. Mintel GNPD [online].
C75 Concealer. Jun. 2016. Mintel GNPD [online].

* cited by examiner

*Primary Examiner* — Shirley V Gembeh
(74) *Attorney, Agent, or Firm* — Abel Schillinger, LLP

(57) ABSTRACT

Cosmetic stick containing: a) one or more UV filters, b) a Fischer-Tropsch wax with a solidification point of 80-85° C. (measured according to ASTM D 938) and a penetration at 25° C. of 0.4-0.9 mm (measured according to ASTM D 1321), the preparation being free from 3-(4-methylbenzylidene)-camphor, 2-hydroxy-4-methoxybenzophenone (INCI: Oxybenzone), 2-ethylhexyl 4-methoxycinnamate (INCI: Octyl Methoxycinnamate) and ethylhexyl-2-cyano-3,3-diphenylacrylate (INCI: Octocrylene).

20 Claims, No Drawings

COSMETIC SUNSCREEN STICK

BACKGROUND OF THE INVENTION

1. Field of the Invention

The present invention relates to a cosmetic stick comprising one or more UV filters and a Fischer-Tropsch wax with a solidification point of 80-85° C. (measured according to ASTM D 938) and a penetration at 25° C. of 0.4-0.9 mm (measured according to ASTM D 1321), the preparation being free of 3-(4-methylbenzylidene)camphor, 2-hydroxy-4-methoxybenzophenone (INCI: Oxybenzone), 2-ethylhexyl 4-methoxycinnamate (INCI: Octyl Methoxycinnamate), and ethylhexyl 2-cyano-3,3-diphenylacrylate (INCI: Octocrylene).

2. Discussion of Background Information

The trend away from aristocratic pallor to "healthy, sporty, brown skin" has been unbroken for years. To achieve this, people expose their skin to sunlight, as this causes pigmentation to develop in the sense of melanin formation. However, the ultraviolet radiation in sunlight has a harmful effect on the skin too. Besides acute damage (sunburn), long-term harm also occurs, such as an increased risk of developing skin cancer if exposed to too much light in the UVB range (wavelength: 280-320 nm). In addition to this, excessive exposure to UVB and UVA radiation (wavelength: 280-320 nm) leads to a weakening of the elastic and collagen fibers in connective tissue. This causes numerous phototoxic and photoallergic reactions and results in premature aging of the skin.

To protect the skin, a range of filter substances that protect against sunlight have therefore been developed that can be used in cosmetic preparations. These UVA and UVB filters are summarized in most developed countries in the form of approved lists such as Annex 7 of the Kosmetikverordnung [German Cosmetics Act].

Nevertheless, despite the multiplicity of sunscreens that are commercially available, it is essential not to forget that these preparations of the prior art have a number of drawbacks.

One preparation form that has been around for quite some time is exemplified by sunscreen sticks such as "Labello sun protect". However, these relatively soft, stick formulations with a penetration hardness at 25° C. of more than 9 mm are suitable only for application to the lips, whereas stick preparations for the facial skin generally need to be considerably harder. On the other hand, persons skilled in the art will be familiar with a multiplicity of liquid lotions that contain UV filters, but are so thin that they can be applied to the facial skin only with applicators (e.g. the fingers). The object was therefore to develop a sunscreen stick that can be spread on the facial skin without problem. This needed to show a penetration hardness at 25° C. in the range of 4 to 7 mm (measured according to DIN 51 579).

A further disadvantage of stick-form sunscreen formulations is that they normally contain 2-ethylhexyl 4-methoxycinnamate (INCI: Octyl Methoxycinnamate) and/or ethylhexyl 2-cyano-3,3-diphenylacrylate (INCI: Octocrylene) as UV filters. These two UV filters, which are both liquid at room temperature (25° C.), are normally needed in order to incorporate the crystalline UV filters 4-(tert-butyl)-4'-methoxydibenzoylmethane, 2,4,6-tris[anilino(p-carbo-2'-ethyl-1'-hexyloxy)]-1,3,5-triazine (INCI: Ethylhexyl Triazone), and 2,4-bis{[4-(2-ethylhexyloxy)-2-hydroxy]phenyl}-6-(4-methoxyphenyl)-1,3,5-triazine (INCI: Bis-Ethylhexyloxyphenol Methoxyphenyl Triazine) into the preparations in "dissolved" form. Without these further UV filters, it is not possible to develop stick-form sunscreens with high sun protection factors (SPF greater than 30, preferably 50 or above) or sticks with adequately high UVA protection.

However, 2-ethylhexyl 4-methoxycinnamate (INCI: Octyl Methoxycinnamate) is not particularly photostable, which can result in a reduction in UV protection if used for long periods. There is also the danger that this process could give rise to photochemical breakdown products that may not be physiologically entirely harmless.

The disadvantage of using Octocrylene is that, despite having been granted marketing authorization by the authorities, Octocrylene is not without controversy, with ratings in some consumer magazines (for example "Öko-Test") having been marked down. The reason given for this negative assessment is because some scientists suspect that this UV filter could potentially be hormonally active. Even though no adverse effects in humans have come to light despite decades of worldwide use of this UV filter in sunscreens, there is a desire among consumers to avoid preparations containing such ingredients.

Moreover, 2-ethylhexyl 4-methoxycinnamate (INCI: Octyl Methoxycinnamate) and ethylhexyl 2-cyano-3,3-diphenylacrylate (INCI: Octocrylene) cause preparations to become sticky and greasy/shiny and are consequently regarded by users as esthetically unattractive.

Last but not least, a problem with a great many sunscreen sticks is that they are insufficiently compatible with the intended packaging material for such sticks, with this resulting in transfer of substances from the packaging material to the preparation and from the preparation to the packaging material.

It was therefore the object of the present invention to develop a stick-form sunscreen preparation (sunscreen stick) with a high sun protection factor (SPF greater than 30, preferably 50 or above) that is free of 2-ethylhexyl 4-methoxycinnamate (INCI: Octyl Methoxycinnamate) and ethylhexyl 2-cyano-3,3-diphenylacrylate (INCI: Octocrylene) and which imparts a matte, rather than greasy/shiny, appearance to the skin, can be spread on the skin easily and gently, and is compatible with the usual packaging materials for stick-form preparations.

SUMMARY OF THE INVENTION

Surprisingly, this object is achieved by a cosmetic stick containing
a) one or more UV filters,
b) a Fischer-Tropsch wax with a solidification point of 80-85° C. (measured according to ASTM D 938) and a penetration at 25° C. of 0.4-0.9 mm (measured according to ASTM D 1321),
with the preparation being free of 3-(4-methylbenzylidene)camphor, 2-hydroxy-4-methoxybenzophenone (INCI: Oxybenzone), 2-ethylhexyl 4-methoxycinnamate (INCI: Octyl Methoxycinnamate), and ethylhexyl 2-cyano-3,3-diphenylacrylate (INCI: Octocrylene).

A further surprise that was unforeseeable by persons skilled in the art was that on application to the skin, the sticks according to the invention, although harder than preparations of the prior art, transferred appreciably more stick substance to the skin than did preparations of the prior art under similar application conditions. The higher and more even amount applied can be visualized with, for example, the method disclosed in DE 102015203509 A1.

It is advantageous in accordance with the invention if the stick according to the invention is characterized in that the preparation contains the Fischer-Tropsch wax in a concentration of at least 10% by weight relative to the total weight of the preparation.

In accordance with the invention, it is preferable if the Fischer-Tropsch wax is present in the formulation in a concentration from 1 to 20% by weight, more preferably from 5 to 20% by weight, and especially preferably from 7 to 15% by weight relative to the total weight of the preparation.

More preferred in accordance with the invention is the Fischer-Tropsch wax with CAS number 8002-74-2, (EINECS number 232-315-6), which has the INCI "Synthetic Wax" and is available from Sasol under the trade name "Sasolwax C80".

It is advantageous in accordance with the invention if the preparation contains one or more UV filters selected from the group of compounds 4-(tert-butyl)-4'-methoxydibenzoylmethane, 2,4,6-tris[anilino(p-carbo-2'-ethyl-1'-hexyloxy)]-1,3,5-triazine (INCI: Ethylhexyl Triazone), 2,4-bis{[4-(2-ethylhexyloxy)-2-hydroxy]-phenyl}-6-(4-methoxyphenyl)-1,3,5-triazine (INCI: Bis-Ethylhexyloxyphenol Methoxyphenyl Triazine), 2-ethylhexyl 2-hydroxybenzoate (INCI: Ethylhexyl Salicylate), and 3,3,5-trimethylcyclohexyl 2-hydroxybenzoate (INCI: Homosalate).

Embodiments of the present invention that are preferred in accordance with the invention are characterized in that the preparation contains 4-(tert-butyl)-4'-methoxydibenzoylmethane in a concentration from 0.1 to 10% by weight, more preferably from 1 to 10% by weight, and especially preferably from 3 to 10% by weight relative to the total weight of the preparation.

Embodiments of the present invention that are preferred in accordance with the invention are additionally characterized in that the preparation contains 2,4,6-tris-[anilino(p-carbo-2'-ethyl-1'-hexyloxy)]-1,3,5-triazine (INCI: Ethylhexyl Triazone) in a concentration from 0.1 to 5% by weight, more preferably from 0.5 to 5% by weight, and especially preferably from 0.5 to 4% by weight relative to the total weight of the preparation.

In addition, it is preferable in accordance with the invention if the preparation contains 2,4-bis{[4-(2-ethylhexyloxy)-2-hydroxy]phenyl}-6-(4-methoxyphenyl)-1,3,5-triazine (INCI: Bis-Ethylhexyloxyphenol Methoxyphenyl Triazine) in a concentration from 0.1 to 10% by weight, more preferably 0.1-7% by weight, and especially preferably from 0.5 to 7% by weight relative to the total weight of the preparation.

The concentration of 2-ethylhexyl 2-hydroxybenzoate (INCI: Ethylhexyl Salicylate) used is, in accordance with the invention, advantageously from 0.1 to 10% by weight, more preferably from 1 to 10% by weight, and especially preferably from 2 to 10% by weight relative to the total weight of the preparation; the concentration of 3,3,5-trimethylcyclohexyl 2-hydroxybenzoate (INCI: Homosalate) used is, in accordance with the invention, advantageously from 0 to 15% by weight relative to the total weight of the preparation.

It is thus preferable, in accordance with the invention, to use a combination of 4-(tert-butyl)-4'-methoxydibenzoylmethane, 2,4,6-tris[anilino(p-carbo-2'-ethyl-1'-hexyloxy)]-1,3,5-triazine (INCI: Ethylhexyl Triazone), 2,4-bis{[4-(2-ethylhexyloxy)-2-hydroxy]phenyl}-6-(4-methoxyphenyl)-1,3,5-triazine (I NCI: Bis-Ethylhexyloxyphenol Methoxyphenyl Triazine), 2-ethylhexyl 2-hydroxybenzoate (INCI: Ethylhexyl Salicylate), and 3,3,5-trimethylcyclohexyl 2-hydroxybenzoate (INCI: Homosalate).

Embodiments of the present invention that are advantageous in accordance with the invention are characterized in that the preparation contains silica and/or titanium dioxide. It is preferable in accordance with the invention if the preparation contains both constituents.

The amount of silica dimethyl silylate used is, in accordance with the invention, advantageously from 0 to 7% by weight relative to the total weight of the preparation.

The amount of titanium dioxide used is, in accordance with the invention, advantageously from 0 to 25% by weight relative to the total weight of the preparation.

To obtain an appealing, stick-form preparation, it is advantageous in accordance with the invention if the preparation comprises one or more waxy constituents selected from the group C20-40 alkyl stearate, cetyl palmitate, myristyl myristate, shea butter (INCI: Butyrospermum Parkii Butter).

Embodiments of the present invention that are preferred in accordance with the invention are characterized in that the preparation contains cetyl palmitate in a concentration from 0.1 to 20% by weight and preferably from 1 to 20% by weight, in each case relative to the total weight of the preparation.

It is additionally advantageous in accordance with the invention if the preparation contains myristyl myristate in a concentration from 0.1 to 20% by weight relative to the total weight of the preparation.

Last but not least, it is advantageous in accordance with the invention if the preparation contains C20-40 alkyl stearate in a concentration from 0.1 to 20% by weight relative to the total weight of the preparation.

The amount of shea butter (INCI: Butyrospermum Parkii Butter) used is, in accordance with the invention, advantageously from 0.1 to 15% by weight relative to the total weight of the preparation.

Stick formulations that are advantageous in accordance with the invention are additionally characterized in that the preparation contains cetyl alcohol and/or stearyl alcohol. The combination of both constituents is preferable in accordance with the invention.

It is advantageous in the sense of the present invention if the preparation contains cetyl alcohol in a concentration from 0.1 to 15% by weight relative to the total weight of the preparation.

In addition, it is advantageous in the sense of the present invention if the preparation contains stearyl alcohol in a concentration from 0.1 to 15% by weight relative to the total weight of the preparation.

To obtain an appealing, cosmetic stick preparation, it is advantageous in the sense of the present invention if the preparation contains one or more oily constituents selected from the group of compounds di-n-butyl adipate, C12-15 alkyl benzoate, butylene glycol dicaprylate/dicaprate (INCI: Butylene Glycol Dicaprylate/Dicaprate), dimethicone.

The concentration of di-n-butyl adipate used is, in accordance with the invention, preferably from 0.1 to 10% by weight relative to the total weight of the preparation.

The concentration of C12-15 alkyl benzoate used is, in accordance with the invention, preferably from 0.1 to 15% by weight relative to the total weight of the preparation.

The concentration of butylene glycol dicaprylate/dicaprate (INCI: Butylene Glycol Dicaprylate/Dicaprate) used is, in accordance with the invention, preferably from 0.1 to 15% by weight relative to the total weight of the preparation.

The concentration of dimethicone used is, in accordance with the invention, preferably from 0.1 to 20% by weight relative to the total weight of the preparation.

The preparation according to the invention may, in accordance with the invention, advantageously comprise antioxidants, for example BHT.

It is additionally advantageous in the sense of the present invention if the preparation according to the invention contains one or more fragrances selected from the group of compounds limonene, citral, linalool, alpha-isomethyl ionone, geraniol, citronellol, 2-isobutyl-4-hydroxy-4-methyl-tetrahydropyran, 2-tert-pentylcyclohexyl acetate, 3-methyl-5-phenyl-1-pentanol, 7-acetyl-1,1,3,4,4,6-hexamethyltetralin, adipic acid diester, alpha-amylcinnamaldehyde, alpha-methyl ionone, amyl C butylphenylmethylpropionalcinnamal, amyl salicylate, amyl cinnamyl alcohol, anisyl alcohol, benzoin, benzyl alcohol, benzyl benzoate, benzyl cinnamate, benzyl salicylate, bergamot oil, bitter orange oil, butylphenylmethylpropioal, cardamom oil, cedrol, cinnamaldehyde, cinnamyl alcohol, citronellyl methylcrotonate, citron oil, coumarin, diethyl succinate, ethyl linalool, eugenol, Evernia furfuracea extract, Evernia prunastri extract, farnesol, guaiac wood oil, hexylcinnamal, hexyl salicylate, hydroxycitronellal, lavender oil, lime oil, linayl acetate, mandarin oil, menthyl PCA, methylheptenone, nutmeg oil, rosemary oil, sweet orange oil, terpineol, tonka bean oil, triethyl citrate, and/or vanillin.

Embodiments of the present invention that are advantageous in accordance with the invention are characterized in that the preparation contains one or more compounds selected from the group of compounds alpha-lipoic acid, folic acid, phytoene, D-biotin, coenzyme Q10, alpha-glycosylrutin, carnitine, carnosine, natural and/or synthetic isoflavonoids, flavonoids, creatine, creatinine, taurine, β-alanine, panthenol, magnolol, honokiol, tocopheryl acetate, dihydroxyacetone; 8-hexadecene-1,16-dicarboxylic acid, glycerylglycose, (2-hydroxyethyl) urea, vitamin E and its derivatives, hyaluronic acid and/or its salts, and/or licochalcone A.

Embodiments of the present invention that are advantageous in accordance with the invention are characterized in that the preparation is free of parabens, methylisothiazolinone, chloromethylisothiazolinone, and DMDM hydantoin.

Comparative Test

| INCI | Ex. 1 | Ex. 2 | Ex. 3 | Ex. 4 | Ex. 5 | Ex. 6 | Ex. 7 |
| --- | --- | --- | --- | --- | --- | --- | --- |
| Synthetic Wax | 11.00 | | | | | | |
| C20-40 Alkyl Stearate | 2.00 | 13.00 | | | | | |
| Microcrystalline Wax | | | 11.00 | | | | |
| Carnauba | | | | 11.00 | | | |
| Hydrogenated Castor Oil | | | | | 11.00 | | |
| Myristyl Myristate | 8.00 | 8.00 | 8.00 | 8.00 | 8.00 | 19.00 | 8.00 |
| C12-15 Alkyl Benzoate | 5.00 | 5.00 | 5.00 | 5.00 | 5.00 | 5.00 | 16.00 |
| Dibutyl Adipate | 2.00 | 2.00 | 2.00 | 2.00 | 2.00 | 2.00 | 2.00 |
| Butylene Glycol Dicaprylate/Dicaprate | 3.00 | 3.00 | 3.00 | 3.00 | 3.00 | 3.00 | 3.00 |
| Dimethicone | 10.04 | 10.04 | 10.04 | 10.04 | 10.04 | 10.04 | 10.04 |
| Cetyl Palmitate | 12.00 | 12.00 | 12.00 | 12.00 | 12.00 | 12.00 | 12.00 |
| *Butyrospermum Parkii* Butter | 8.00 | 8.00 | 8.00 | 8.00 | 8.00 | 8.00 | 8.00 |
| Cetearyl Alcohol | 5.00 | 5.00 | 5.00 | 5.00 | 5.00 | 5.00 | 5.00 |
| Stearyl Alcohol | 5.00 | 5.00 | 5.00 | 5.00 | 5.00 | 5.00 | 5.00 |
| Silica Dimethyl Silylate | 1.00 | 1.00 | 1.00 | 1.00 | 1.00 | 1.00 | 1.00 |
| Perfume | q.s. | q.s. | q.s. | q.s. | q.s. | q.s. | q.s. |
| Homosalate | 9.00 | 9.00 | 9.00 | 9.00 | 9.00 | 9.00 | 9.00 |
| Ethylhexyl Salicylate | 4.75 | 4.75 | 4.75 | 4.75 | 4.75 | 4.75 | 4.75 |
| Bis-Ethylhexyloxyphenol Methoxyphenyl Triazine | 4.00 | 4.00 | 4.00 | 4.00 | 4.00 | 4.00 | 4.00 |
| Ethylhexyl Triazone | 3.50 | 3.50 | 3.50 | 3.50 | 3.50 | 3.50 | 3.50 |
| Butyl Methoxydibenzoylmethane | 4.75 | 4.75 | 4.75 | 4.75 | 4.75 | 4.75 | 4.75 |
| Titanium Dioxide (nano) | 0.82 | 0.82 | 0.82 | 0.82 | 0.82 | 0.82 | 0.82 |
| Silica | 0.15 | 0.15 | 0.15 | 0.15 | 0.15 | 0.15 | 0.15 |
| Texture vs. Base 1 | Base 1 | Oily | Oily | Sticky | Sticky | Oily and sticky | Oily and sticky |
| Penetration [mm] | 5.8 | 7.4 | 9.4 | 7.6 | 7.1 | 13 | 15.3 |

DETAILED DESCRIPTION OF EMBODIMENTS OF THE INVENTION

Examples

The examples below are intended to illustrate the present invention, without restricting it. Unless otherwise stated, all amounts, proportions, and percent contents are relative to the weight and total amount/total weight of the preparations.

| INCI | Ex. 8 | Ex. 9 | Ex. 10 | Ex. 11 | Ex. 12 | Ex. 13 |
| --- | --- | --- | --- | --- | --- | --- |
| Synthetic Wax | 11.00 | 11.00 | 11.00 | 11.00 | 11.00 | 9.00 |
| C20-40 Alkyl Stearate | 2.00 | 2.00 | 2.00 | 2.00 | 2.00 | 5.00 |
| Myristyl Myristate | 12.00 | 8.00 | 15.00 | 8.00 | 5.00 | 8.00 |
| C12-15 Alkyl Benzoate | 10.00 | 5.00 | 5.00 | 5.00 | 5.00 | 5.00 |
| Dibutyl Adipate | 7.00 | 7.00 | 2.00 | 2.00 | 2.00 | 1.00 |
| Butylene Glycol Dicaprylate/Dicaprate | 7.00 | 3.00 | 3.00 | 3.00 | 3.00 | 1.00 |

-continued

| INCI | Ex. 8 | Ex. 9 | Ex. 10 | Ex. 11 | Ex. 12 | Ex. 13 |
|---|---|---|---|---|---|---|
| Dimethicone | ad 100 | ad 100 | ad 100 | ad 100 | ad 100 | ad 100 |
| Cetyl Palmitate | 12.00 | 12.00 | 5.00 | 15.00 | 12.00 | 12.00 |
| *Butyrospermum Parkii* Butter | 8.00 | 8.00 | 8.00 | 8.00 | 8.00 | 8.00 |
| Cetearyl Alcohol | 5.00 | 5.00 | 5.00 | 5.00 | 5.00 | 5.00 |
| Stearyl Alcohol | 5.00 | 5.00 | 5.00 | 5.00 | 5.00 | 5.00 |
| Silica Dimethyl Silylate | 0.00 | 5.00 | 1.00 | 1.00 | 1.00 | 1.00 |
| Perfume | q.s. | q.s. | q.s. | q.s. | q.s. | q.s. |
| Homosalate | 0.00 | 0.00 | 9.00 | 9.00 | 9.00 | 9.00 |
| Ethylhexyl Salicylate | 3.00 | 4.50 | 4.75 | 4.75 | 4.75 | 4.75 |
| Bis-Ethylhexyloxyphenol Methoxyphenyl Triazine | 1.00 | 3.00 | 4.00 | 4.00 | 4.00 | 4.00 |
| Ethylhexyl Triazone | 0.50 | 2.00 | 3.50 | 3.50 | 3.50 | 3.50 |
| Butyl Methoxydibenzoylmethane | 3.00 | 3.50 | 4.75 | 4.75 | 4.75 | 4.75 |
| Titanium Dioxide (nano) | 0.00 | 0.00 | 0.82 | 0.82 | 0.82 | 0.82 |
| Silica | 0.00 | 0.00 | 0.15 | 0.15 | 0.15 | 0.15 |

What is claimed is:

1. A cosmetic stick preparation, wherein the preparation comprises
(a) one or more UV filters, and
(b) a Fischer-Tropsch wax having a solidification point, measured according to ASTM D 938, of 80-85° C., and a penetration at 25° C., measured according to ASTM D 1321, of 0.4-0.9 mm,
and wherein the preparation is free of 3-(4-methylbenzylidene)camphor, 2-hydroxy-4-methoxybenzophenone, 2-ethylhexyl 4-methoxycinnamate and ethylhexyl 2-cyano-3,3-diphenylacrylate.

2. The cosmetic stick preparation of claim 1, wherein the preparation comprises the Fischer-Tropsch wax in a concentration of from 1% to 20% by weight relative to a total weight of the preparation.

3. The cosmetic stick preparation of claim 1, wherein the preparation comprises the Fischer-Tropsch wax in a concentration of from 5% to 20% by weight relative to a total weight of the preparation.

4. The cosmetic stick preparation of claim 1, wherein the preparation comprises the Fischer-Tropsch wax in a concentration of from 7% to 15% by weight relative to a total weight of the preparation.

5. The cosmetic stick preparation of claim 1, wherein the preparation comprises one or more UV filters selected from 4-(tert-butyl)-4'-methoxydibenzoylmethane, 2,4,6-tris[anilino(p-carbo-2'-ethyl-1'-hexyloxy)]-1,3,5-triazine, 2,4-bis{[4-(2-ethylhexyloxy)-2-hydroxy]phenyl}-6-(4-methoxyphenyl)-1,3,5-triazine, 2-ethylhexyl 2-hydroxybenzoate, and 3,3,5-trimethylcyclohexyl 2-hydroxybenzoate.

6. The cosmetic stick preparation of claim 1, wherein the preparation comprises at least three UV filters selected from 4-(tert-butyl)-4'-methoxydibenzoylmethane, 2,4,6-tris[anilino(p-carbo-2'-ethyl-1'-hexyloxy)]-1,3,5-triazine, 2,4-bis{[4-(2-ethylhexyloxy)-2-hydroxy]phenyl}-6-(4-methoxyphenyl)-1,3,5-triazine, 2-ethylhexyl 2-hydroxybenzoate, and 3,3,5-trimethylcyclohexyl 2-hydroxybenzoate.

7. The cosmetic stick preparation of claim 1, wherein the preparation comprises 4-(tert-butyl)-4'-methoxydibenzoylmethane, 2,4,6-tris[anilino(p-carbo-2'-ethyl-1'-hexyloxy)]-1,3,5-triazine, 2,4-bis{[4-(2-ethylhexyloxy)-2-hydroxy]phenyl}-6-(4-methoxyphenyl)-1,3,5-triazine, 2-ethylhexyl 2-hydroxybenzoate, and 3,3,5-trimethylcyclohexyl 2-hydroxybenzoate.

8. The cosmetic stick preparation of claim 1, wherein the preparation comprises 4-(tert-butyl)-4'-methoxydibenzoylmethane in a concentration of from 0.1% to 10% by weight relative to a total weight of the preparation.

9. The cosmetic stick preparation of claim 1, wherein the preparation comprises 2,4,6-tris[anilino(p-carbo-2'-ethyl-1'-hexyloxy)[-1,3,5-triazine in a concentration of from 0.1% to 5% by weight relative to a total weight of the preparation.

10. The cosmetic stick preparation of claim 1, wherein the preparation comprises 2,4-bis{[4-(2-ethylhexyloxy)-2-hydroxy]-phenyl}-6-(4-methoxyphenyl)-1,3,5-triazine in a concentration from 0.1% to 10% by weight relative to a total weight of the preparation.

11. The cosmetic stick preparation of claim 1, wherein the preparation further comprises silica and/or titanium dioxide.

12. The cosmetic stick preparation of claim 1, wherein the preparation further comprises one or more waxy constituents selected from C20-40 alkyl stearate, cetyl palmitate, myristyl myristate, shea butter.

13. The cosmetic stick preparation of claim 1, wherein the preparation comprises cetyl palmitate in a concentration of from 0.1% to 20% by weight relative to a total weight of the preparation.

14. The cosmetic stick preparation of claim 1, wherein the preparation comprises myristyl myristate in a concentration of from 0.1% to 20% by weight relative to a total weight of the preparation.

15. The cosmetic stick preparation of claim 1, wherein the preparation comprises C20-40 alkyl stearate in a concentration of from 0.1% to 20% by weight relative to a total weight of the preparation.

16. The cosmetic stick preparation of claim 1, wherein the preparation further comprises cetyl alcohol and/or stearyl alcohol.

17. The cosmetic stick preparation of claim 1, wherein the preparation further comprises one or more oily constituents selected from di-n-butyl adipate, C12-15 alkyl benzoate, butylene glycol dicaprylate/dicaprate, dimethicone.

18. The cosmetic stick preparation of claim 1, wherein the preparation is free of parabens, methylisothiazolinone, chloromethylisothiazolinone and DMDM hydantoin.

19. The cosmetic stick preparation of claim 1, wherein the preparation further comprises C20-C40 alkyl stearate, myristyl myristate, C12-C15 alkyl benzoate, dibutyl adipate, butylene glycol dicaprylate/dicaprate, dimethicone, cetyl palmitate, shea butter, cetyl alcohol, and stearyl alcohol.

20. A cosmetic stick, wherein the stick comprises the preparation of claim 1.

* * * * *